United States Patent [19]

Anderson

[11] Plant 4,318

[45] Oct. 17, 1978

[54] NECTARINE TREE (44-G-520)

[75] Inventor: Frederic W. Anderson, Merced, Calif.

[73] Assignee: Reedley Nursery, Inc., Reedley, Calif.

[21] Appl. No.: 867,371

[22] Filed: Jan. 6, 1978

[51] Int. Cl.[2] ..... A01H 5/03

[52] U.S. Cl. ..... Plt./41

[58] Field of Search ..... Plt./41

*Primary Examiner*—Robert E. Bagwill

*Attorney, Agent, or Firm*—Roger B. Webster

[57] ABSTRACT

A nectarine tree which is large to medium in size, vigorous to medium in vigor, upright to spreading in growth, foliated with large to medium size, lanceolate, acutely pointed leaves having a crenate margin, medium length petiole, and alternate, reniform glands, and a regular and productive bearer of large to medium size, uniform, symmetrical, globose, clingstone fruit having yellow skin substantially overspread with red, yellow flesh, and a pit cavity which is red with the red streaked lightly into the flesh about the pit cavity.

1 Drawing Figure

BACKGROUND OF THE VARIETY

1. Field of the Invention

Over a substantial number of years I have engaged in an extensive and continuing plant breeding program at my experimental nursery and orchard located near Le Grand, Merced County, Calif.; one purpose of such program being to provide improved varieties of fruit trees. The present variety of nectarine tree resulted from my endeavors in the conduct of such plant breeding program; such variety being embraced by Class 41, Plants, of the U.S. Patent Office Manual of Classification.

2. Prior Varieties

Among the existent varieties of nectarine trees which are known to me, I make particular reference to the Late Le Grand (U.S. Plant Pat. No. 1,035) and the Regal Grand (U.S. Plant Pat. No. 1,751) mentioned hereinafter for the purpose of comparison.

ORIGIN OF THE VARIETY

The present variety of nectarine tree was originated by me in my experimental nursery and orchard, located as aforesaid, as a cross between the Niagara (U.S. Plant Pat. No. 2,883) and the Autumn Gold (U.S. Plant Pat. No. 3,478). In maturity, the original tree of the variety produced by such cross evidenced certain novel and desirable characteristic for ultimate commercial production, and I, therefore, undertook asexual reproduction of said variety for such purpose.

ASEXUAL REPRODUCTION OF THE VARIETY

The present variety of nectarine tree was asexually reproduced by me, in my said experimental orchard, by top-working on mature trees, and—in maturity—such reproductions ran true to the original tree in all respects.

SUMMARY OF THE VARIETY

The herein-claimed new and distinct variety of nectarine tree is large to medium in size, vigorous to medium in vigor, upright to spreading in growth, foliated with large to medium size, lanceolate, acutely pointed leaves having a crenate margin, medium length petiole, and alternate, reniform glands, and a regular and productive bearer of large to medium size, uniform, symmetrical, globose, clingstone fruit having yellow skin substantially overspread with red, yellow flesh, and a pit cavity which is red with the red streaked lightly into the flesh about the pit cavity.

The herein-claimed new and distinct variety of nectarine tree is particularly characterized, as to novelty, by fruit which ripens a few days later than the Late Le Grand and a few days earlier than the Regal Grand; the fruit—as further compared with said prior varieties—being, on the average, slightly smaller in size but more uniform, more attractive in appearance by reason of greater red exterior color, and of better eating quality.

BRIEF DESCRIPTION OF THE DRAWING

The drawing is an illustration, by photographic reproduction in color, of a twig with leaves, and separate fruit; one of the latter being half cut away to expose the flesh and the stone.

DESCRIPTION OF THE VARIETY

The botanical details of this new and distinct variety of nectarine tree—with color definitions (except those in common color terms) referenced to Maerz and Paul Dictionary of Color—are as follows:

Tree:
- *Size.*—Large to medium.
- *Vigor.*—Vigorous to medium.
- *Growth.*—Upright to spreading.
- *Production.*—Productive.
- *Bearing.*—Regular bearer.

Trunk:
- *Size.*—Medium.
- *Texture.*—Medium.

Branches:
- *Size.*—Medium.
- *Texture.*—Medium.

Leaves:
- *Size.*—Large to medium. Average length — 6½". Average width — 1¼".
- *Form.*—Lanceolate. Acutely pointed.
- *Thickness.*—Medium.
- *Texture.*—Smooth.
- *Color.*—Top side — Medium green (23-J-8). Under Side — Lighter green (22-J-6).
- *Margin.*—Crenate.

*Petiole.*—Medium length. Medium thickness.

*Glands.*—Number and position — usually 4 — 2 on blade and 2 on petiole. Alternate. Medium size. Reniform.

Flowers:

*Blooming period.*—Medium, as compared with other varieties.

*Size.*—Large.

*Color.*—Pink.

Fruit:

*Maturity when described.*—Eating ripe (Sept. 7, 1977).

*Date of first picking.*—Aug. 28, 1977.

*Date of last picking.*—Sept. 7, 1977.

*Size.*—Uniform. Large to medium. Average diameter axially — $2\frac{5}{8}''$. Average transversely in suture plane — $2\frac{5}{8}''$.

*Form.*—Uniform. Symmetrical. Globose.

*Suture.*—Distinct. Deep. Extends from base to beyond apex, with slight depression beyond pistil point.

*Ventral surface.*—Rounded strongly.

*Cavity.*—Rounded.

*Base.*—Rounded.

*Apex.*—Short. Depressed.

*Pistil point.*—Wanting.

Skin:

*Thickness.*—Medium.

*Texture.*—Tough to medium.

*Tenacity.*—Tenacious to flesh.

*Tendency to crack.*—None noted.

*Down.*—Wanting.

*Color.*—Yellow (10-K-5) substantially overspread with red (6-L-5) shading to darker red (7-L-5), with substantial mottling and some streaking.

Flesh:

*Juice.*—Abundant to moderate.

*Texture.*—Firm. Crisp. Meaty.

*Ripens.*—Evenly.

*Flavor.*—Subacid.

*Aroma.*—Wanting.

*Eating quality.*—Fair to good.

*Color.*—Yellow (9-L-4). Surface of pit cavity — Red (5-L-6) with red lightly streaked into the flesh.

Stone:

*Type.*—Clingstone.

*Size.*—Medium. Average length — $1\frac{3}{8}''$. Average breadth — $1''$. Average thickness — $\frac{5}{8}''$.

*Form.*—Globose — oblong.

*Base.*—Straight.

*Apex.*—Rounded.

*Sides.*—Equal.

*Tendency to split.*—Slight.

*Color.*—Reddish brown (8-L-6).

Use: Market. Dessert.

Keeping quality: Good.

Resistance to insects and diseases: No unusual susceptibilities noted.

Shipping quality: Good.

The nectarine tree and its fruit herein described may vary in slight detail due to climatic and soil conditions under which the variety may be grown; the present description being of the variety as grown in the Central Valley of California.

I claim:

1. A new and distinct variety of nectarine tree, substantially as illustrated and described, particularly characterized by clingstone fruit which ripens a few days later than the Late Le Grand and a few days earlier than the Regal Grand; the fruit, as further compared with said prior varieties, being, on the average, slightly smaller in size but more uniform, more attractive in appearance by reason of greater red exterior color, and of better eating quality.

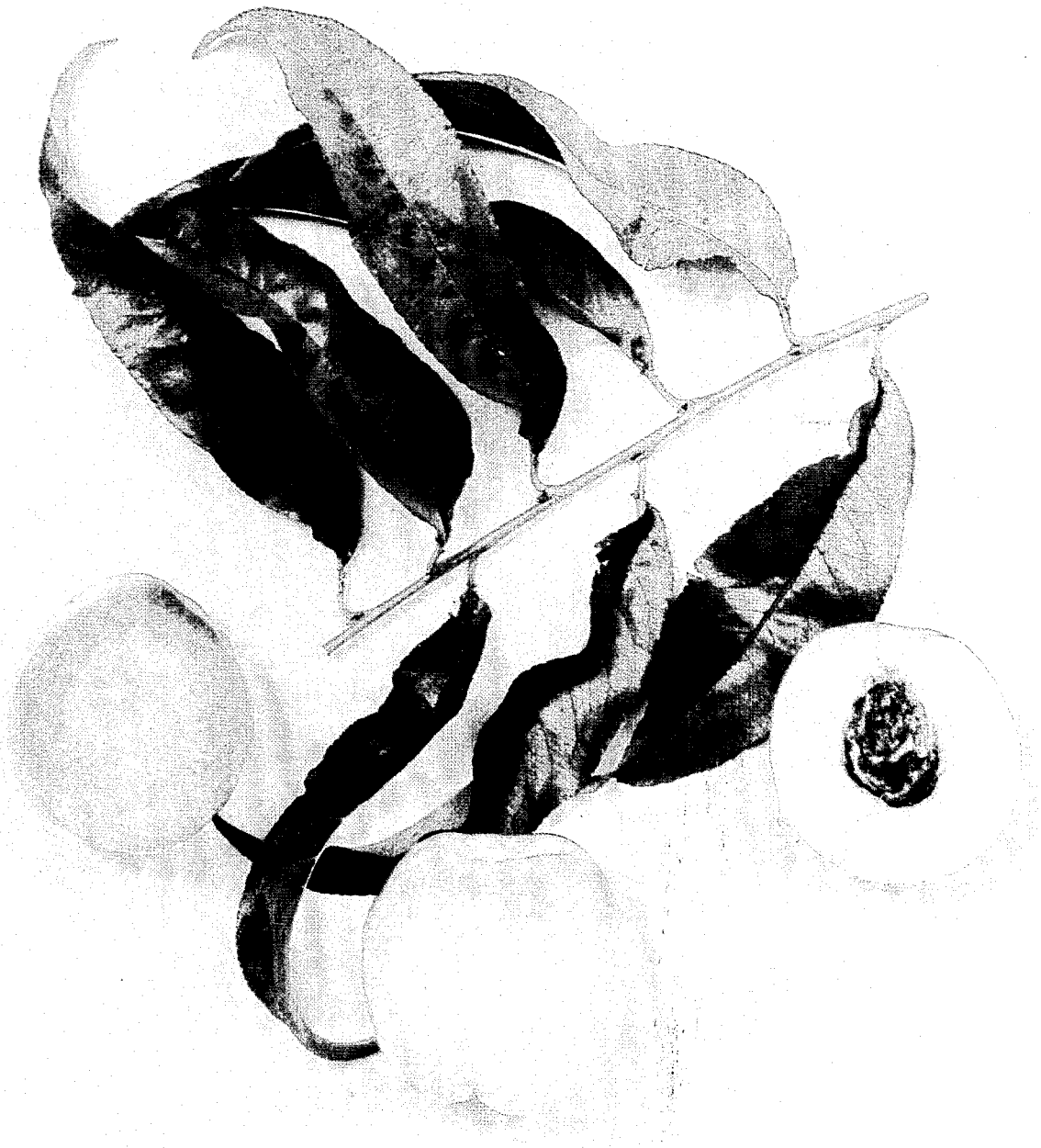

* * * * *